(12) United States Patent
Stuehle et al.

(10) Patent No.: US 9,277,851 B2
(45) Date of Patent: Mar. 8, 2016

(54) VIDEO ENDOSCOPE

(71) Applicant: OLYMPUS WINTER & IBE GMBH, Hamburg (DE)

(72) Inventors: Sebastian Stuehle, Hamburg (DE); Sebastian Jungbauer, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 14/425,658

(22) PCT Filed: Jul. 18, 2013

(86) PCT No.: PCT/EP2013/002141
§ 371 (c)(1),
(2) Date: Mar. 4, 2015

(87) PCT Pub. No.: WO2014/037069
PCT Pub. Date: Mar. 13, 2014

(65) Prior Publication Data
US 2015/0216395 A1    Aug. 6, 2015

(30) Foreign Application Priority Data
Sep. 5, 2012  (DE) .......................... 10 2012 017 499

(51) Int. Cl.
*A61B 1/05* (2006.01)
*A61B 1/00* (2006.01)
*G02B 23/24* (2006.01)

(52) U.S. Cl.
CPC ........... *A61B 1/00124* (2013.01); *A61B 1/0011* (2013.01); *A61B 1/00018* (2013.01); *A61B 1/05* (2013.01); *A61B 1/051* (2013.01); *G02B 23/2484* (2013.01); *Y10T 29/49117* (2015.01)

(58) Field of Classification Search
CPC .... A61B 1/00124; A61B 1/0011; A61B 1/05; A61B 1/051; A61B 1/00018; G02B 23/2484; H01R 24/38; H01R 24/86
See application file for complete search history.

(56) References Cited

U.S. PATENT DOCUMENTS

| 4,831,456 A | 5/1989 | Takamura |
| 6,095,970 A | 8/2000 | Hidaka et al. |

(Continued)

FOREIGN PATENT DOCUMENTS

| DE |   19806984 A1 | 8/1998 |
| DE | 102004023866 B3 | 2/2006 |

(Continued)

OTHER PUBLICATIONS

International Search Report dated Nov. 6, 2013 issued in PCT/EP2013/002141.

(Continued)

*Primary Examiner* — John P Leubecker
(74) *Attorney, Agent, or Firm* — Scully, Scott, Murphy & Presser, PC

(57) ABSTRACT

A video endoscope including: a tube forming an interior, a window formed at a distal end of the tube; an image sensor; a support in the interior for supporting the image sensor, said image sensor viewing through the window; a conductor arranged on the support, the conductor electrically connecting the image sensor, and a closing wall at a proximal end of the tube through which a pin extends, said pin being in contact with the conductor on the support, wherein the support abuts an inner face of the closing wall such that a surface region of the support on which the conductor is mounted contacts the closing wall at an angle at the point where the pin is located such that a portion of the pin protrudes into the interior and rests in a parallel manner on the surface region of the support and makes contact with the conductor.

10 Claims, 8 Drawing Sheets

(56) References Cited

U.S. PATENT DOCUMENTS

| | | | |
|---|---|---|---|
| 6,293,910 B1 * | 9/2001 | Yamakita | A61B 1/0011 600/110 |
| 6,805,665 B1 * | 10/2004 | Tatsuno | A61B 1/05 600/101 |
| 2003/0169333 A1 * | 9/2003 | Yazawa | A61B 1/00188 348/65 |
| 2004/0176661 A1 * | 9/2004 | Futatsugi | A61B 1/05 600/110 |
| 2012/0029287 A1 * | 2/2012 | Wieters | A61B 1/0011 600/133 |
| 2013/0303850 A1 * | 11/2013 | Stuehle | A61B 1/00124 600/109 |
| 2014/0066711 A1 * | 3/2014 | Farin | A61B 1/0676 600/109 |

FOREIGN PATENT DOCUMENTS

| | | | |
|---|---|---|---|
| DE | 102010044786 A1 | 3/2012 | |
| JP | 1-222579 A | 9/1989 | |
| JP | 2006-68260 A | 3/2006 | |
| WO | WO 2012031644 A1 * | 3/2012 | A61B 1/00071 |

OTHER PUBLICATIONS

English Abstract of WO 12/031,644 A1, dated Mar. 15, 2012.

* cited by examiner

VIDEO ENDOSCOPE

CROSS-REFERENCE TO RELATED APPLICATION

The present application is based upon and claims the benefit of priority from PCT/EP2013/002141 filed on Jul. 18, 2013, which claims benefit to DE 10 2012 017 499.3 filed on Sep. 5, 2012, the entire contents of each of which are incorporated herein by reference.

BACKGROUND

1. Field

The present invention generally relates to endoscopes, and to a video endoscope of the type referred to in claim 1.

2. Prior Art

DE 10 2004 023 866 B3 and DE 10 2010 044 786 A1 show generic video endoscopes, in which the image sensor in each case is held by a rigid support, which in the case of the first-mentioned document is formed as dimensionally stable board and in the case of the second-mentioned document as a rod-shaped support body with conductor strips arranged on the surface. At the end of the support opposite the image sensor this is in both cases connected to the pins passing though the closing wall, which project outwards beyond the closing wall and there may be contacted for connection with the strip conductors.

In both known structures the ends of the pins protruding into the space enter at right angles the local front surface of the support and can be fixed there in a conventional soldering technique. This requires time-consuming, costly manufacturing steps.

SUMMARY

An object of the present invention is to improve the aforementioned video endoscope structurally and in particular with regard to manufacturing costs.

According to the invention the surface region of the support, on which a strip conductor is situated, touches the closing wall at the point at which a pin protrudes inwards. The pin therefore lies parallel to the surface of the support. This results in new opportunities for the configuration of the contacting, so that the pin can be contacted easily and in particular extensively with the strip conductor. Thus the production costs can be reduced and contacting problems avoided.

Advantageously according to claim 2 the angle between the surface region and the inner wall is 90°. In this way the pin can pass vertically through the closing wall in the usual way, in order to be able to then abut this exactly parallel to the surface of the support also standing vertically to the closing wall in the usual way. This results in the possibility of extensive contact between the pin and strip conductor, wherein the contacting surface is largely randomly selectable over the length of the contacted pin region.

Advantageously the features of claim 3 are thereby provided. The proven structure of DE 10 2010 044 786 A1 results.

Advantageously according to claim 4 the contacting between strip conductor and pin is designed so that the strip conductor passes over the pin. This results in particular in the possibility in one of the usual manufacturing methods of the strip conductor abutting the surface of the support and the pin, as a metal coating, for example, which is separated by vapor deposition in a vacuum or electrolytically, for example. This results in a cost-effective and particularly secure contacting.

The support, as is clear from the aforementioned documents, may be connected, for example, to the closing wall via the pins. Advantageously according to claim 5, however, it is fixed directly to the closing wall. This allows a very secure and strong connection. The contacting points do not have to ensure the mechanical connection and are therefore unburdened.

The support and closing wall must be made of insulating materials, since they must support the strip conductors and the pins and thereby avoid short circuits. Advantageously according to claim 6 the support and closing wall are integrally formed and thus from the same material, such as a suitable ceramic or a suitable plastic. The subsequent connection step between the two parts is saved by the integral design and a very strong connection results. The manufacturing costs can also be reduced in this way. They can be manufactured, for example, in a plastic molding process or in a ceramic sintering process, wherein the pins passing through the closing wall are formed in the manufacture.

The system tube usually consists of metal, that is, a material that differs from the material of the support and the closing wall. Advantageously according to claim 7, however, all three parts are integral and thus also formed from the same insulating material. This results in the possibility of the whole arrangement being integrally manufactured, which results in technical manufacturing advantages.

The closing wall can be integrally formed, but may also advantageously according to claim 8 be divided into a distal and a proximal piece, the distal part of which is attached to the support. These pieces can be assembled together on the separating plane. Manufacturing and cost advantages result from this.

According to claim 9, in the manufacture of the video endoscope, it is advantageous that at a contacting point between pin and strip conductor first the pin is arranged abutting the surface of the support and then the strip conductor is affixed to the surface of the support and to the pin. Thus the contacting can be manufactured with the pin at the same time as its joining to the support in a coating application process suitable for the manufacture of the strip conductor without the need for a separate manufacturing step, such as, for example, a soldering.

DETAILED DESCRIPTION

Figure 1:
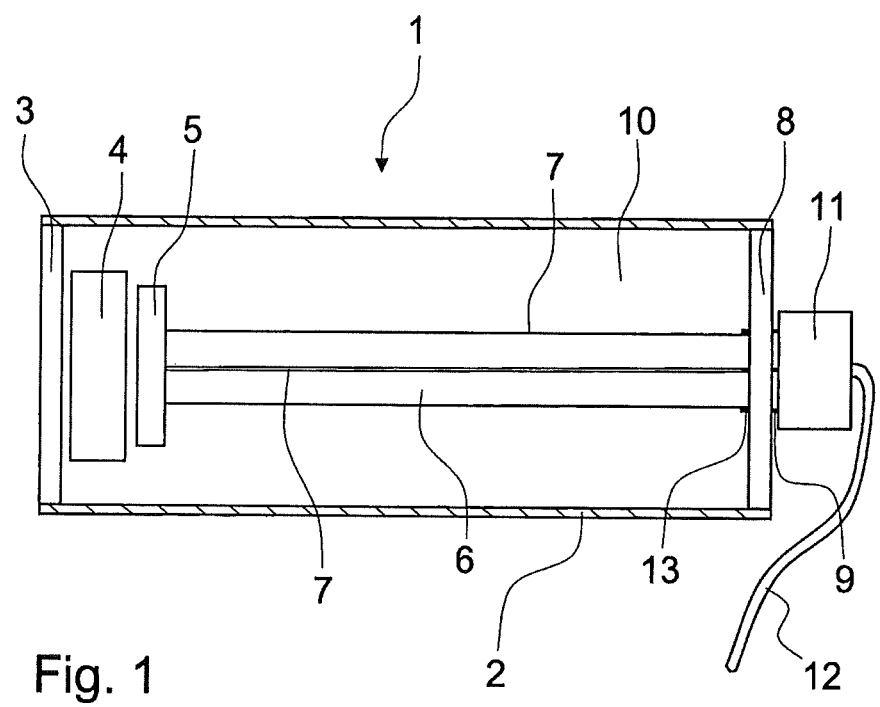
FIG. 1 shows a longitudinal section through a video endoscope according to the invention with a closing wall at one end, FIG. 2 an enlarged section from FIG. 1 in the region of the closing wall.

FIG. 1 shows a video endoscope 1, which is independently usable in the shown form or can also be incorporated into an endoscopic device.

The video endoscope 1 shown has an elongated system tube 2 of a round cross-section in the embodiment, which can be manufactured in the usual design from a suitable stainless steel. The system tube 2 is closed at the distal end with a window 3, on the inner face of which an object lens 4 is arranged. An image sensor 5 observes the work area lying distally from the video endoscope 1 through the object lens 4 and the window 3.

The image sensor 5 is arranged at the distal end of a rod-shaped support 6, which is of a round cross-section in the embodiment. It supports on its surface a plurality of conductor paths, such as strip conductors 7 extending in the longitudinal direction of the support 6. In the drawing, an embodiment is shown in which the support 6 supports four strip conductors circumferentially spaced at 90°.

The proximal end of the system tube 2 is closed with a closing wall 8, on which, as shown in FIG. 1, the support 6 is fixed in abutment. The closing wall 8 is penetrated by pins 9, which are contacted at their ends projecting into the interior 10 with the strip conductors 7.

The ends of the pins 9 projecting outwards from the closing wall 8 can be contacted, for example, by the connector 11 shown in FIG. 1, which is connected via a cable 12 to an image processing device, not shown, which is connected to the image sensor 5 via a plurality of electrical conductors. Via these conductors the image sensor can be supplied with electricity, for example, and can emit its video signal outwards.

Figure 2:
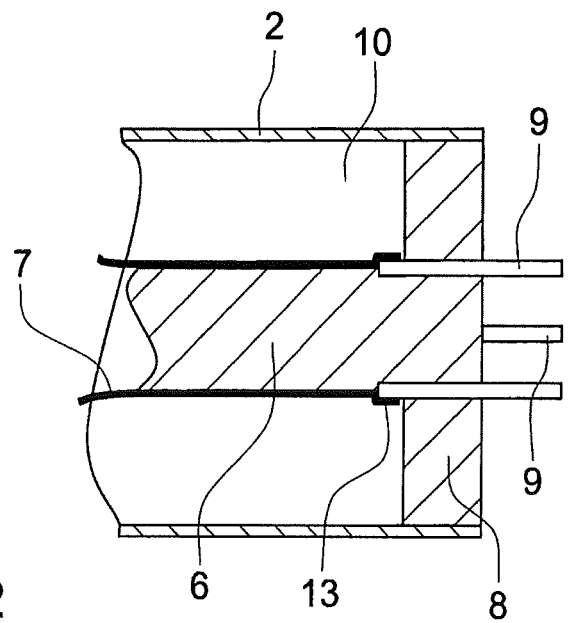

As already mentioned, the support 6 at the proximal end is connected to the closing wall 8. As FIG. 2 shows in detail, these two parts can be designed in a single piece and thus from the same material, e.g. a suitable plastic or a suitable ceramic. Important requirements are electrical insulation properties, so that the various pins 9 or strip conductors 7 are well insulated from each other.

FIG. 2 shows that the support 6 has its axis perpendicular to the plane of the closing wall 8. The result is that the surface of the support 6 touches the inner face of the closing wall 8 at right angles everywhere.

As FIG. 2 shows, the pins 9 are parallel to each other and perpendicular to the closing wall 8. They are therefore parallel to the axis of the support 6 and can, in the case of a suitable arrangement, as shown in FIG. 2, be arranged horizontally with their inner ends projecting into the closing wall 8 in the interior 10 parallel and flat on the outer face of the support 6. As FIG. 2 shows, they can also be slightly embedded in the surface of the support 6.

As FIG. 2 also shows, the strip conductors 7 extend to the surface of the support 6 and into the end region to the contacting point 13 via the pins 9.

The manufacture of the structure of FIG. 2 is preferably carried out so that first the unit consisting of the support 6 and closing wall 8 is integrally manufactured as a plastic molded body or as a ceramic sintered body. In this way the pins 9 are incorporated which, for example, are held in the plastic injection mold for injection molding. In the case of ceramic sintering the pins can mounted in the green body, that is, in the unfired material. A gas-tight embedding is to be ensured.

Subsequently, the strip conductors are applied, which can be applied in a known manner electrochemically or by vapor deposition, or sputtering. The strip conductors are simultaneously deposited on the surface of the support 6 and on the pins 9, which results in a particularly secure contacting.

The parts of the video endoscope not shown in FIG. 2 must be mounted and finally pushed over the system tube 2 and attached sealingly at the edge of the closing wall 8, for example, by bonding, soldering, crimping or the like.

Figure 3:
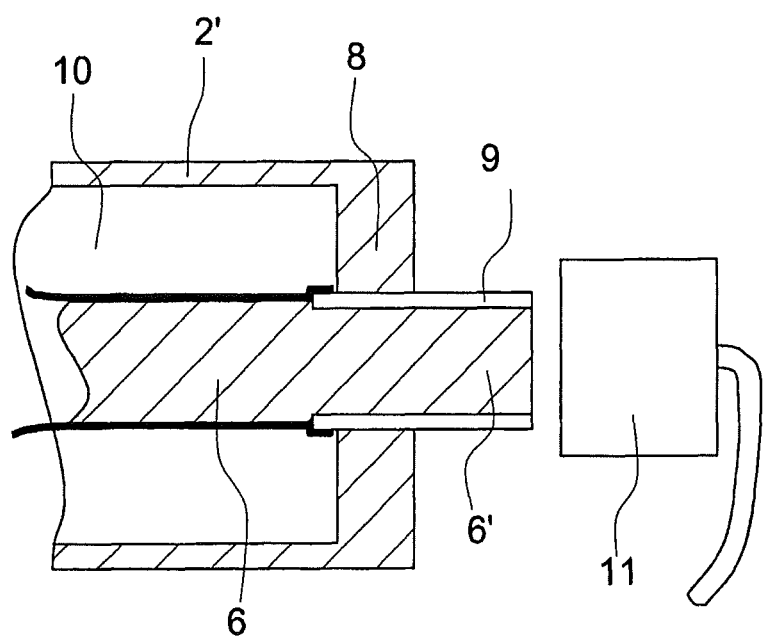
FIG. 3 shows a view corresponding to FIG. 2 in another embodiment.

FIG. 3 shows a variant embodiment of FIG. 2. Here the system tube 2 is replaced by a tube 2', which is integrally formed with the support 6 and the closing wall 8. So the whole basic structure can be manufactured as a single piece. Thereby production problems, such as tightness, are mitigated and costs reduced.

In comparison with FIG. 2, it is clear that in the embodiment of FIG. 3 a projection 6' configured according to the support 6 is arranged outside the closing wall 8 in alignment with the support 6. On this are located the pins 9, also arranged on the outer face, as is the case in the interior 10 with the support 6.

The arrangement projecting outwards to the closing wall 8 with the projection 6' and the adjacent pins 9 results in a structure which is well suited as a male connector, which can be coupled with the female connector 11. The external male connector 6', 9, is very stable and secures the structure against bending of pins, for example.

In the embodiments of FIGS. 2 and 3 the closing wall 8 is integrally formed. To clarify this, the inner part of the structure of FIG. 2 is shown again in FIG. 4, that is, in the omitted system tube 2. During the assembly, the construction unit shown in FIG. 4 is produced first and then according to FIG. 2 connected to the system tube 2.

Figure 4:
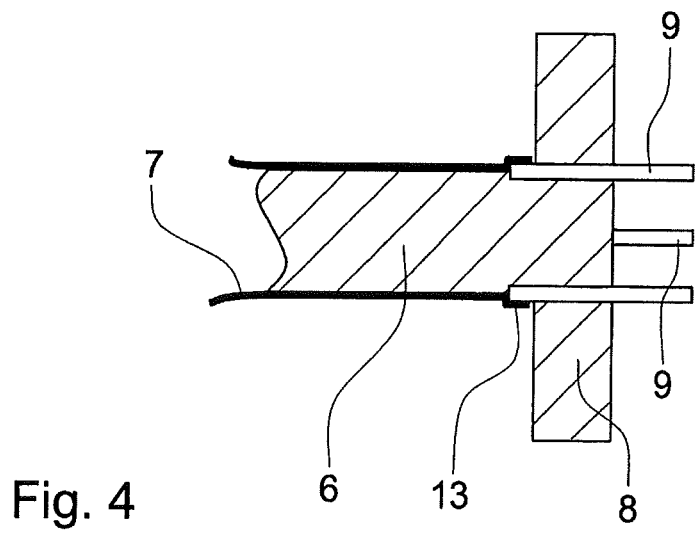
FIG. 4 shows the structure of FIG. 2, but without the system tube.
Figure 5:
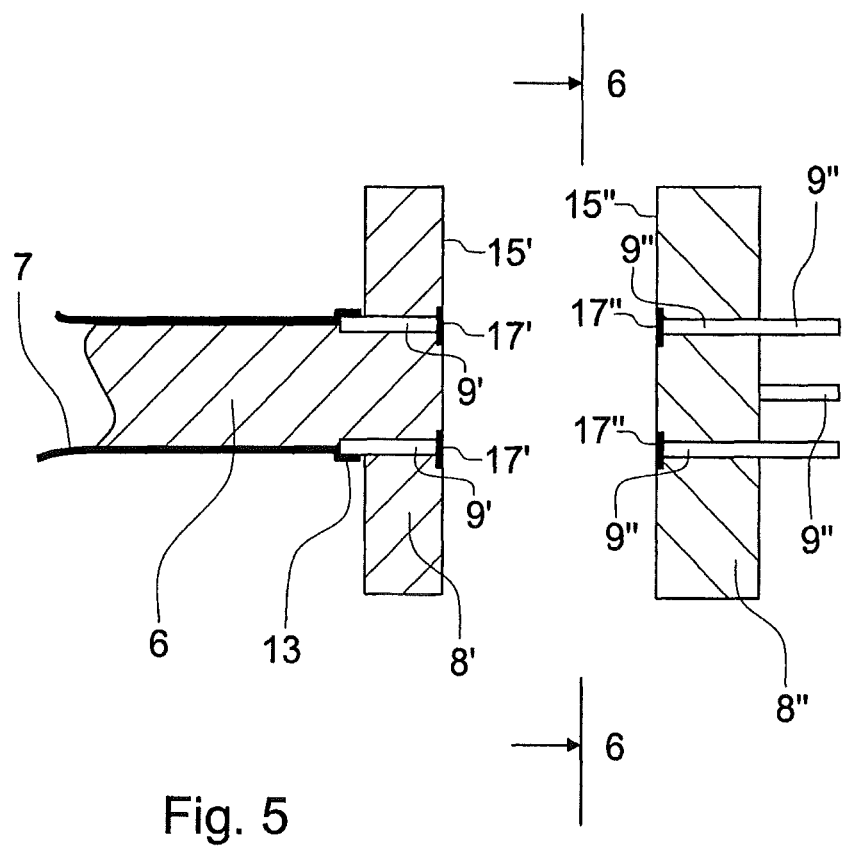
FIG. 5 shows the structure of FIG. 4 with the closing wall divided into two pieces.
Figure 6:
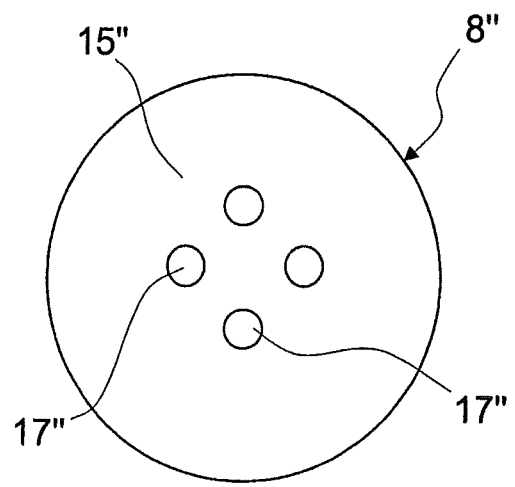
FIG. 6 shows a section along line 6-6 in FIG. 5.

FIGS. 5 and 6 show a variant embodiment in which, with respect to the structure shown in FIG. 4, it is evident that the closing wall 8 of FIG. 4 is now divided into two segments 8' and 8". The segments 8' and 8" have oppositely oriented planar surfaces 15' and 15", with which the segments 8' and 8" are able to be linked. They can then be connected by bonding, for example, and then in the manner described above inserted into the system tube 2 and there soldered at the edge.

As FIG. 5 shows, the pins passing through the closing wall are also in each case divided into pieces 9' and 9". The ends of the pin pieces 9' and 9", which lie in the planar surfaces 15' and 15", support contact plates 17' and 17" there, which come into contact during the attachment of the segments 8' and 8" and can be soldered together or conductively bonded.

Figure 7:
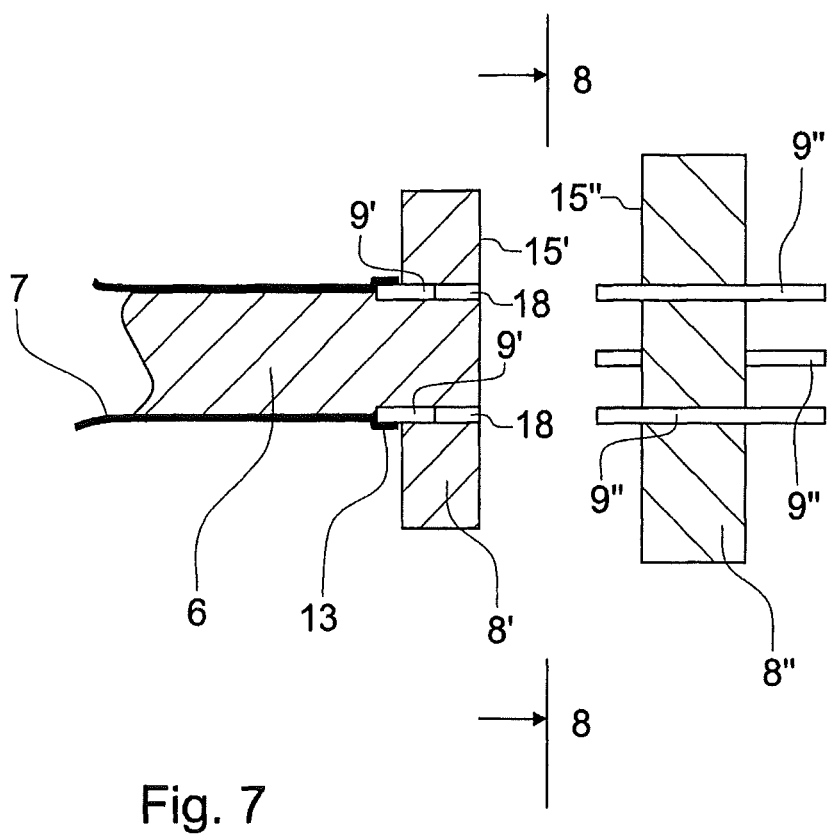
FIG. 7 shows the structure of FIG. 5 in a variant embodiment and FIG. 8 shows a section along line 8-8 in FIG. 7.
Figure 8:
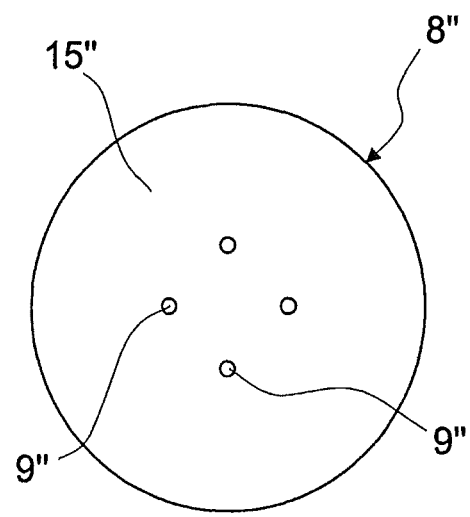

FIGS. 7 and 8 show a variant embodiment of the embodiment of FIGS. 5 and 6. The same reference numerals are used. The structural differences are as follows:

The distal segment 8' of the closing wall is smaller in diameter. This is sufficient for the present purposes. The attachment in system tube 2 is made to segment 8".

The pieces 9' of the pins lying in the distal segment 8' are recessed below the planar surface 15'. The pin parts 9" in the proximal segment 8" are formed to project in the distal direction over the planar surface 15" and can be immersed in bores 18 during the attachment of the segments 8' and 8" to each other, which are formed above the pin parts 9'.

This results during the assembly in a helpful form-fitting engagement of the pin parts 9' in the bores 18. The pin parts 9' and 9" meet at the bottom of the bores 18 and can be conductively bonded or soldered there.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A video endoscope comprising:
   a system tube forming an interior which is gas-tightly enclosed,
   a window formed at a distal end side of the system tube;

an image sensor;

a support disposed in the interior for supporting the image sensor, said image sensor being configured to view from the interior through the window;

at least one conductor path arranged on the support, the at least one conductor path electrically connecting the image sensor, and a closing wall formed at a proximal end side of the system tube through which at least one pin extends in a sealed manner, said at least one pin being in contact with the at least one conductor path on the support in the interior, wherein the support abuts an inner face of the closing wall such that a surface region of the support on which the at least one conductor path is mounted contacts the closing wall at an angle at the point where the at least one pin is located such that a portion of the at least one pin protrudes into the interior in a parallel manner on the surface region of the support and makes contact with the at least one conductor path.

2. The video endoscope according to claim 1, wherein the surface region of the support contacts a surface of the closing wall at a right angle.

3. The video endoscope according to claim 2, wherein the support is formed as a rod standing perpendicular to the closing wall, and the at least one pin passes through the closing wall parallel to an axis of the rod.

4. The video endoscope according to claim 1, wherein the conductor path is formed over an inner end region of the at least one pin.

5. The video endoscope according to claim 1, wherein the support is attached to the closing wall.

6. The video endoscope according to claim 5, wherein the support is integrally formed with the closing wall.

7. The video endoscope according to claim 6, wherein the closing wall and support are integrally formed with the system tube.

8. The video endoscope according to claim 1, wherein the closing wall is divided into distal and proximal wall segments contacting each other on a plane lying transverse to the at least one pin, of which the distal wall segment is attached to the support.

9. The video endoscope according to claim 1, wherein the at least one conductor path comprises at least one conductor strip.

10. A process for the manufacture of the video endoscope according to claim 4, comprising:

arranging the at least one pin with the inner end region adjacent to the surface region of the support; and applying the conductor path to the surface region of the support and to the inner end region of the pin.

\* \* \* \* \*